United States Patent [19]

Kramer et al.

[11] 4,287,416
[45] Sep. 1, 1981

[54] METHOD OF DETERMINING FATIGUE AND STRESS CORROSION DAMAGE

[75] Inventors: Irvin R. Kramer, Baltimore, Md.; Sigmund Weissman, Metuchen, N.J.; Robert N. Pangborn, State College, Pa.

[73] Assignee: The United States of America as represented by the Secretary of the Navy, Washington, D.C.

[21] Appl. No.: 135,065

[22] Filed: Mar. 28, 1980

[51] Int. Cl.$^3$ ............................................. G01N 23/20
[52] U.S. Cl. .................................... 250/273; 250/272
[58] Field of Search ................ 250/272, 273, 274, 275

[56] References Cited

U.S. PATENT DOCUMENTS

| 2,079,900 | 5/1937 | Cohn | 250/273 |
| 2,462,374 | 2/1949 | Firth | 250/272 |
| 4,095,103 | 6/1978 | Cohen et al. | 250/272 |

OTHER PUBLICATIONS

Biedermann et al., "Rapid Determination of Dislocation Densities in Crystals", *IBM Tech. Disclosure Bull.*, vol. 14, No. 1, Jun. 1971.

Cullity, B. D., *Elements of X-ray Diffraction*, pp. 292–295, Addison–Wesley Pub. Co., Oct. 1978.

*Primary Examiner*—Alfred E. Smith
*Assistant Examiner*—T. N. Grigsby
*Attorney, Agent, or Firm*—R. S. Sciascia; L. A. Marsh; W. W. Randolph

[57] ABSTRACT

A method of determining the amount of fatigue or stress-corrosion damage occurring in a member includes the step of matching the target material of the x-ray tube with the material of the member such that x-rays from such target material are capable of penetrating beyond the work hardened surface layer of the member. Since the work hardened surface layer extends up to a depth of from about 100 to 200 micrometers in most metallic materials, the x-ray radiation should at least penetrate to a depth of from about 200 to about 400 micrometers to provide x-ray diffraction line intensity profiles from which the excess dislocation density for the material can be determined. The ratio of the average excess dislocation density of the member to the critical excess dislocation density at failure is equivalent to the fatigue or stress-corrosion damage that has occurred to the member.

6 Claims, 4 Drawing Figures

METHOD OF DETERMINING FATIGUE AND STRESS CORROSION DAMAGE

The invention described herein may be manufactured and used by or for the Government of the United States of America for any governmental purposes without the payment of any royalties thereon or therefor.

BACKGROUND OF THE INVENTION

The present invention generally relates to an insitu, nondestructive technique for determining the amount of fatigue and stress corrosion damage occurring in a material before the onset of a propagating crack. More particularly, the method comprises the utilization of x-ray diffraction techniques to determine the average excess dislocation density over a certain depth range in the surface layer of the material and comparing such value with a predetermined critical value of the excess dislocation density for the material.

In general, fatigue is a term used to describe the behavior of materials under repeated cycles of stress or strain which cause a deterioration of the material that results in progressive cracking and failure of such material. Conventional fatigue testing machines, as disclosed in U.S. Pat. No. 2,729,096 for example, are utilized to apply alternating stresses and displacements to a test specimen until the specimen fails after a number of repetitive loading cycles. Such fatigue machines are normally designed to apply either an axial load, bending or flexural loads, torsional loads or a combination thereof, wherein the test specimen in such machines are normally loaded by applying either a constant deflection or a constant load thereto. However, since the test specimens utilized in fatigue testing machines are normally simplified models of the actual structural or machine element and since the stress conditions applied by the fatigue testing machines do not approximate the stress-time or strain-time history of the element, the fatigue strength determined thereby is usually not a close approximation of the actual fatigue strength of the element.

X-ray diffraction techniques have been developed to determine various physical properties of materials, as exemplified by U.S. Pat. Nos. 3,934,138; 4,095,103; 4,125,771 and 4,128,762 which are directed to methods of determining the residual stress in materials. However, past attempts to use x-ray diffraction line broadening to measure fatigue damage were unsuccessful, as noted for example by C. S. Barrett on pages 337–338 of *Structure of Metals; Crystallographic Methods, Principles and Data*, published by McGraw-Hill in 1943. In these prior investigations it was reported that the x-ray diffraction lines of the immediate surface broadened as the material was initially fatigued, but that after a small fraction (eg. about 15%) of the fatigue life of the material, the diffraction line broadening tended to remain virtually unaltered, both in extent and intensity, throughout the remainder of the fatigue life of the material. Since these prior investigations assumed that the structural changes in the interior or bulk region and at the surface were the same, the fatigue damage and the remaining fatigue life of the materials were inaccurate. In actuality, it was discovered, as noted in the *Determination of Prefracture Fatigue Damage*, by I. Kramer, S. Weissmann and R. Pangborn and published by the David W. Taylor Naval Ship Research and Development Center (DTNSRDC), Bethesda, Md., in January 1980, (Report DTNSRDC 80/006) and herein incorporated by reference, that the structural changes in the bulk region and at the surface were different. For example, it was found that the surface of the material work hardened, as measured by the increase in the dislocation density, to a much greater extent than the interior or bulk region.

SUMMARY OF THE INVENTION

Accordingly, the present invention provides an accurate, insitu method of determining the amount of fatigue and stress corrosion damage occurring in a material. The foregoing is generally accomplished by utilizing an x-ray diffraction technique wherein the target material of the x-ray tube is selected such that the x-ray beam penetrates a predetermined distance into the specimen material. From the x-ray diffraction line intensity profile of the irradiated material, the width of the diffraction line intensity profile at one-half of the maximum intensity value provides a measure of the excess dislocation density for the material. Also, the shape of the x-ray diffraction line profile can be used to determine the excess dislocation density for the material. By comparing the excess dislocation density value after fatiguing, with the critical excess dislocation density value at failure of the material, the amount of fatigue damage to the material can be determined. The excess dislocation density values from x-ray diffraction lines may also be utilized to analyze the amount of stress corrosion damage which occurs to a material in a given environment.

Therefore, it is an object of this invention to provide a rapid, insitu method of determining the fatigue and stress-corrosion damage in materials, thus eliminating the necessity for extensive installations of expensive and bulky testing machines.

Another object of the present invention is the provision of a nondestructive method for accurately determining the fatigue and stress-corrosion damage in a structural element irrespective of the particular size and shape of the structural element.

A further object of this invention is to provide a method for determining the fatigue and stress-corrosion damage in a material without knowing its prior stress and fatigue history.

Still another object of the present invention is to provide a method for determining the fatigue and stress-corrosion damage in a material regardless of whether the applied stress is tensile, compressive, bending, torsional or any combination thereof.

BRIEF DESCRIPTION OF THE DRAWINGS

The novel features which are believed to be characteristic of this invention are set forth with particularity in the appended claims. The invention itself, however, both as to its organization and the method disclosed herein, together with further objects and advantages thereof, may be best understood by reference to the following description taken in conjunction with the accompanying drawings, in which:

DETAILED DESCRIPTION OF THE INVENTION

Figure 1:
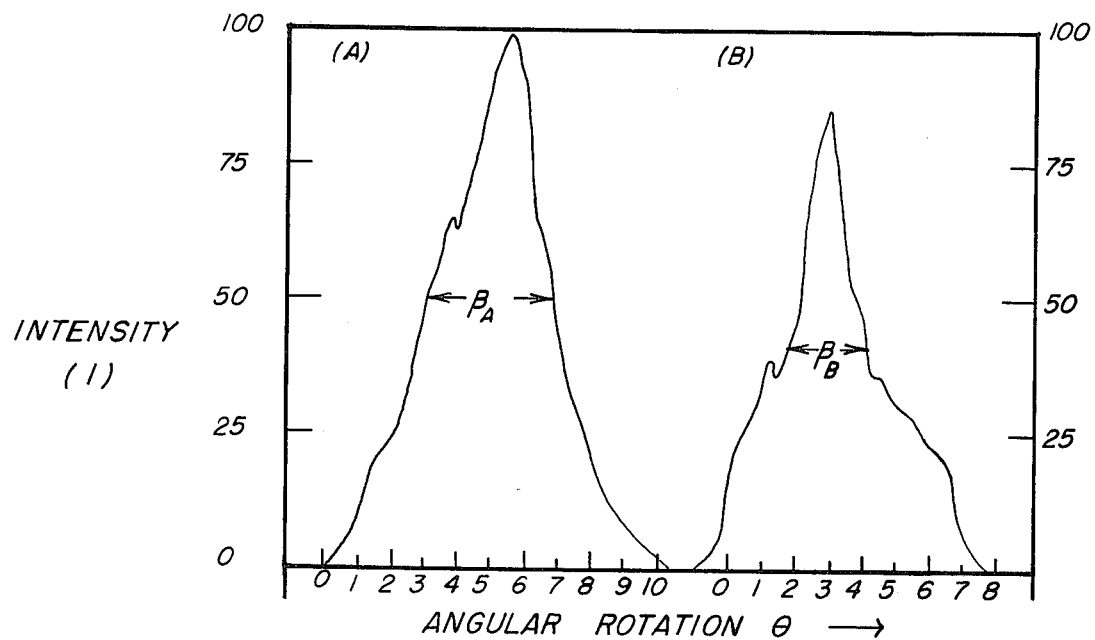
FIG. 1 shows x-ray diffraction line intensity profile curves of a material.

According to the insitu, nondestructive method of the present invention, an appropriate x-ray diffraction technique is used wherein the target material of the x-ray tube is selected so that the radiation therefrom is at least capable of penetrating a critical depth into the material, and preferably therebeyond. Although the critical depth for a given material will vary according to the chemical composition, the critical depth for metals will be on the order of about 100 to 400 micrometers. By applying various diffraction techniques, such as disclosed by C. S. Barrett in the *Structure of Metals, Crystallographic Methods, Principles and Data*, published by McGraw-Hill Inc. (1954), a series of x-ray diffraction line intensity profiles can be obtained for the material, from the surface to the maximum depth of penetration of the x-ray beam. From the x-ray diffraction line intensity profiles, such as shown in FIG. 1, parameters related to the fatigue and stress corrosion damage, such as the excess dislocation density, can be determined. The excess dislocation density is defined as the difference between the number of positive and negative dislocations per unit area. The relationship of the average excess dislocation density occurring in the material to the critical excess dislocation density occurring at failure of the material provides an accurate measure of its fatigue life and the stress corrosion damage occurring therein.

An application of the abovementioned method utilizing a particular x-ray diffraction technique, as further disclosed in the aforementioned report *Determination of Prefracture Fatigue Damage*, distributed by the David W. Taylor Naval Ship R&D Center, Bethesda, Md., on cyclically stressed 2024 aluminum alloy specimens enabled the prediction of both the fatigue life and ultimate failure of the specimens with high accuracy. In one test, a 2024 aluminum alloy specimen was axially loaded initially at 25 ksi for 18,000 cycles, then at 31 ksi for 28,500 cycles, and then at 36 ksi for 15,000 cycles. The x-ray diffraction analysis utilizing a molybdenum target was performed after the specimen was fatigued at 36 ksi. The data predicted that if the specimen was fatigued at 41 ksi, failure would occur at a total of 72,190 cycles. Under such loading conditions, the specimen actually failed at 69,000 cycles and thus, the prediction of fatigue life was very close to the actual value.

From the x-ray diffraction spots, a plurality of diffraction line intensity profiles or curves can be plotted. An example of two diffraction intensity profile curves is generally shown in FIG. 1, wherein the y coordinate represents the intensity (I) of the reflected x-ray beam from the test specimen and the x coordinate represents the diffraction angle (Bragg angle, $\theta$) of the x-ray beam. As can be seen from FIG. 1, the maximum intensity occurs at the Bragg angle $\theta$ with the intensity distribution ranging over a region $\Delta\theta$. By analyzing the x-ray diffraction line profile curves and accordingly the various (hkl) reflections, a representative statistical parameter ($\bar{\beta}$) of the dislocation defect structure of the grain population can be obtained. $\beta$ is defined as the width of an x-ray intensity profile curve at half of the maximum intensity, as shown by values $\beta_a$ and $\beta_b$ in FIG. 1.

According to one approach, the excess dislocation density ($\rho$) is obtained from the relationship, $\rho = \beta^2/9b^2$ where $\beta$ is obtained as shown in FIG. 1, and b is the magnitude of the Burgers vector for the material.

A more extensive discussion of this relationship is set forth by P. B. Hirsch in Prog. Met. Phy. (1956), volume 6, page 283. Thus, from the width $\beta$ at half of the intensity maximum in the diffraction line intensity profiles the average excess dislocation density value of the material over a predetermined depth can be determined. The depth to which the x-rays penetrate to produce the x-ray diffraction pattern over such depth range is dependent upon the wavelength of the x-rays and the material being irradiated. Another approach for determining the excess dislocation density $\rho$ of an intensity profile curve, and accordingly the resulting average value $\bar{\rho}$, is the Warren-Averbach approach, as noted by B. E. Warren and B. L. Averbach in the Journal of Applied Physics (1950), volume 1, page 591. Briefly, this approach utilizes the shape of the intensity profile curves to determine the excess dislocation density $\rho$ values.

Figure 3:
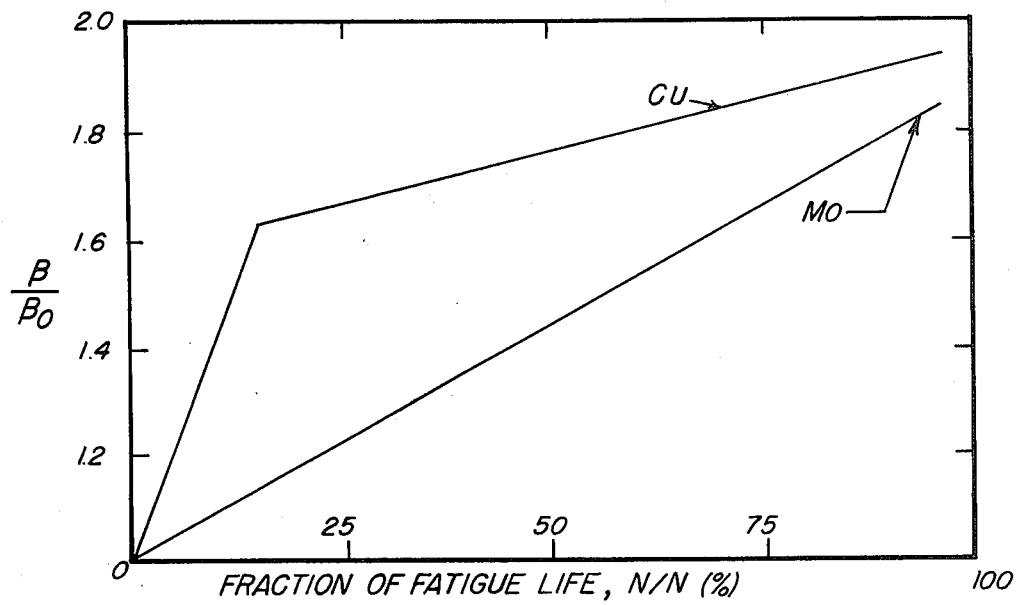
FIG. 3 is a diagram of the fatigue damage in a material as a function of the excess dislocation density occurring therein when measured at the surface with Cu radiation and to a depth of about 350 micrometers.

It was observed that during fatigue cycling the surface material, which usually extends up to a depth of from about 100 to about 200 micrometers in metallic materials, work hardens more rapidly than the bulk or interior material. The surface of the material acts as a barrier to oppose the motion of the dislocations so that after a small fraction of the fatigue life of the structural element, the value of average excess dislocation density $\bar{\rho}$ at the surface rapidly approaches the critical average excess dislocation density $\bar{\rho}^*$ for the structural element. The critical value $\bar{\rho}^*$ for the structural element. The critical value $\rho^*$ is defined as the average excess dislocation density value for the structural element at fatigue failure, such as when a propagating crack is generated therein. By utilizing an x-ray tube having a target which produces x-rays which only penetrate the surface material (e.g. to a depth of about 10 micrometers) such as with a copper or a chromium target for an aluminum alloy material, the critical value $\bar{\rho}^*$ can only be approximated, but cannot be determined accurately. For example, as shown by the curve for copper radiation in FIG. 3 which depicts $\beta$ and $\rho$ values for the surface of an aluminum alloy element, there is an initial steep rise in the curve until about 20% of the fatigue life of the element and, thereafter, the curve is almost horizontal until failure, with a small increase in the average excess dislocation density $\rho$ of the surface material. However, by irradiating the interior or bulk of the structural element with an x-ray radiation that penetrates beyond the hardened surface layer, the resultant curve is much steeper and $\rho^*$ can be accurately determined.

Also, in practice the (1) $\bar{\rho}$ value for the surface layer and the interior or bulk region of the material and the (2) $\bar{\rho}^*$ value for the surface layer alone, which, as aforementioned, approximates the $\bar{\rho}^*$ value for the specimen, can be obtained by carrying out a simple exposure sequence using an x-ray radiation of appropriate penetrability. For a 2024 aluminum alloy element, a molybdenum target was used and the diffractions of the x-ray radiation from the element were recorded on multiple films that were separated by copper foil screens of appropriate thickness. The first film was used to record the contribution from both the surface layer and the bulk portion of the material and the second film, owing to the suppression of the weak intensities from the bulk region by the interposed copper screens, registered only the intense reflections emanating from the surface of the element. Thus, the critical value of excess dislocations $\rho^*$ can be determined from the convergence of the two curves pertaining to the hardened surface layer and the bulk of the structural element, respectively.

The fraction of fatigue damage occurring in a material can be generally expressed by the relationship $N/N_F$ wherein N is the fatigue damage to the material expressed as a number of fatigue cycles and $N_F$ is number of fatigue cycles to failure of the element. Generally, $N/N_f = \rho/\bar{\rho}^*$ and hence $\rho/\bar{\rho}^* = \beta^2/\beta^{*2}$ so that the amount of fatigue damage to a structural or machine element can be found by determining the appropriate $\rho$ and $\beta$ values for the material.

Proper utilization of the values of the excess dislocation density $\rho$ to determine the fatigue and stress-corrosion damage to a structural element is dependent upon the recognition that dislocations at the surface and in the bulk of the material behave differently during fatigue. The surface work hardens more rapidly than the bulk or interior region during fatiguing and stress-corrosion and a surface layer of appropriate depth was found to oppose the motion of the dislocations by providing a barrier layer to support a piled-up array of dislocations of like sign. When the barrier layer attains a strength sufficient to support a critical amount of excess dislocations $\rho$, fatigue (or stress-corrosion) fracture of the material occurs. It was also found that this critical value was independent of the prior stress amplitude, fatigue history and environment. However, the fatigue strength of a specimen cannot be determined and predicted with certainty if the x-ray radiation does not penetrate sufficiently deep to pass through the work hardened surface layer of the material. As may be seen from FIG. 3, for example, application of copper radiation, which has energy to penetrate only a small fraction (approximately less than 10 percent) of the work hardened surface layer, gave rise to a rapid increase of $\beta/\beta_o$ between $N/N_F=0$ and $N/N_F=20$ percent, and only a very gradual increase for $N/N_F$ between 20 and 90 percent. Beyond $N/N_F=90$ percent, $\beta/\beta_o$ becomes critical and fracture occurs rather rapidly. $\beta_o$ is the excess dislocation density for an unfatigued material, the ratio $\beta/\beta_o$ provides a measure of the increase in the excess dislocation as the material is fatigued. Because of the broken and nearly horizontal configuration of the copper radiation curve in FIG. 3, the fatigue damage values for $N/N_F$ greater than about 25% do not provide an accurate measure of the fatigue damage in a structural element. In contrast, the steep, single stage curve in FIG. 3 was derived from the use of a molybdenum target in the x-ray tube that produced penetrating molybdenum radiation, which irradiated the grains in the bulk of the specimen as well as those in the surface layer. Thus by using x-ray radiation which penetrates beyond the surface of the material an accurate measure of the average excess dislocation density $\bar{\rho}$ in the material can be determined.

Figure 2:
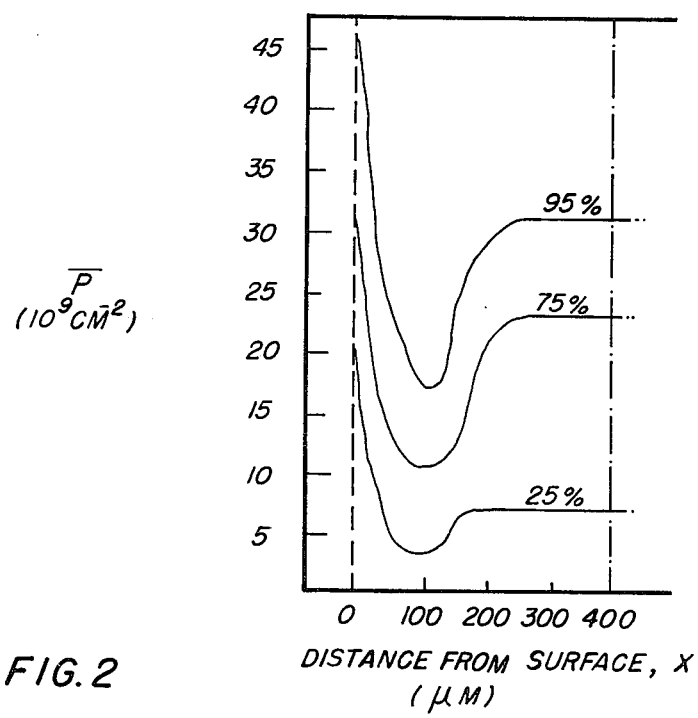
FIG. 2 is a depth profile curve of the material showing the excess dislocation density as a function of a predetermined depth in the material.

The curves in FIG. 2 show the depth profiles for the excess dislocation density $\rho$ for an aluminum alloy material fatigued up to 25%, 75% and 95% of the fatigue life of the material. Each curve was prepared by fatiguing the machine or structural element to an appropriate amount of its fatigue life and then sequentially irradiating the surface with shallow penetrating radiation to determine the $\beta$ and $\rho$ values thereabout. These values were obtained as a function of depth by removing an appropriate amount of surface material to expose the underlying material. As shown in FIG. 2, the $\rho$ values decrease to a minimum value at about 100 micrometers and then increase and attain a constant value at a depth of about 250 micrometers. Also, although the $\rho$ values in the interior of the aluminum element increased with the number of fatigue cycles, such values never approached the $\rho$ values at the surface. By integrating the curves in FIG. 2, from a depth of about 400 micrometers to the surface a linear fatigue damage curve, such as shown for the molybdenum radiation in FIG. 3, can be attained which provides an accurate measure of the actual fatigue damage occurring in a machine or structural element. It was discovered that failure occurs independently of stress, fatigue history and environment when the excess dislocation density, as determined with molybdenum radiation for example, attains critical $\rho^*$ or $\beta^*$ values.

Figure 4:
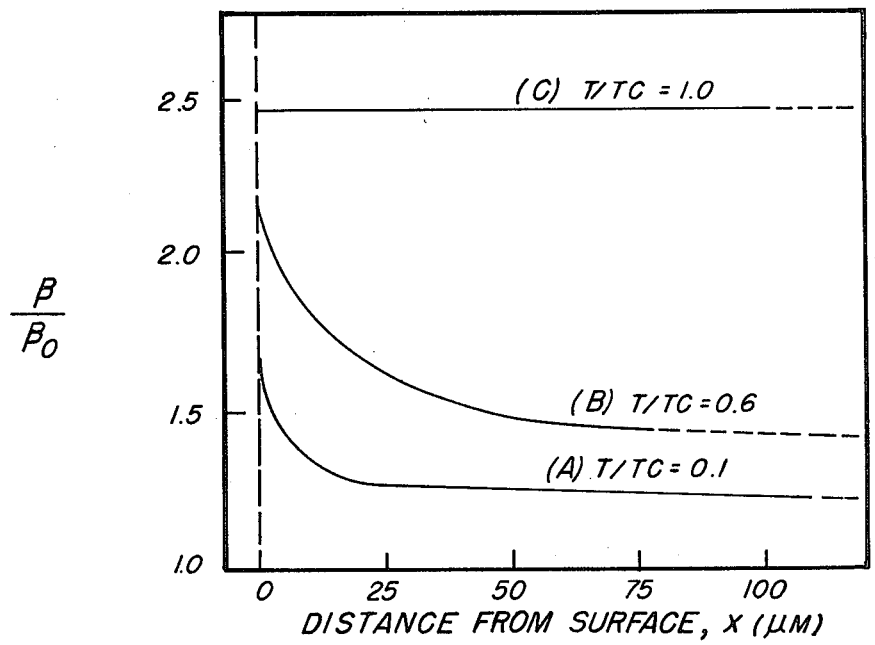
FIG. 4 is a diagram of the stress corrosion damage in a material as a function of the excess dislocation density occurring therein.

FIG. 4 depicts the depth profiles of a structural element for various stages of stress corrosion. Generally, stress corrosion is the preferential attack and failure of a material under an applied stress in a corrosive environment where the stress factor, if taken alone, would not have caused failure. As shown in the figure for values of $t/t_c$ less than 1, the curves are similar to the shape of the curves in FIG. 2, with the exception that the troughs are absent. The value $t_c$ represents the critical failure time that would elapse before a structural element loaded according to the appropriate stress corrosion conditions would fail and t represents the actual period of time that the structural element is placed in such conditions. Accordingly, since the behavior of the dislocations in a structural element under fatigue closely parallels a structural element in a stress corrosion environment, the technique of determining the $\bar{\beta}$ and $\bar{\rho}$ values over an appropriate depth range in the surface layer of a material is essentially analogous. For example, the $\beta/\beta_o$ ratio, and thus the value for $\beta$, assumes a constant value, in this particular instance, at a depth of about 50 to 100 micrometers. For most materials in stress corrosion environments $\beta$ should have a constant value at a depth of from about 100 to 400 micrometers.

The major purpose for measuring the amount of fatigue or stress-corrosion damage in a structural member is to determine whether it should be removed or replaced to prevent failure of the structure due to fracture of the member. The fatigue or stress-corrosion damage occurring in a structural member is generally determined as follows:

(1) Assuming that the member has undergone previous fatigue or stress-corrosion damage, x-ray radiation of shallow penetrability is applied to the member so that only the work hardened surface thereof is irradiated. From the x-ray diffraction line intensity profiles of the surface material, the critical excess dislocation density $\rho^*$ for the structural member at failure can be determined.

(2) A target material of an x-ray tube is then selectively matched with the material comprising the structural element so that the x-ray radiation therefrom is capable of penetrating beyond the work hardened surface layer of the structural member. Since the work hardened surface layer extends up to a depth of from about 100 to 200 micrometers, the x-ray radiation should at least penetrate to a depth of from about 200 to about 400 micrometers to provide data from which $\rho$ and $\beta$ for the structural member can be determined. For example, the excess dislocation density $\rho$ of the member may be determined by analyzing the x-ray diffraction intensity profiles for each (0, 0, 1), according to the Warren-Averbach approach.

(3) The ratio of the average excess dislocation density of the member $\bar{\rho}$ over the penetration range of the x-rays to the critical excess dislocation density at failure provides an accurate measure of the fatigue or stress-corrosion damage that has occurred in the member.

What is claimed is:

1. A method of determining the fatigue damage to a structural member which has undergone fatigue loading comprising the steps of:
   irradiating the surface of the member with x-rays of shallow penetrability to provide an x-ray diffraction line intensity profile of the member to a depth of about 10 micrometers, said x-ray diffraction line intensity profile providing a measure of the critical excess dislocation density of the member at fatigue failure of the member; and
   selectively matching the target material of an x-ray tube with the material of the structural member such that x-rays from the target material are capable of penetrating beyond the work hardened surface layer of the member to provide an x-ray diffraction line intensity profile of the member over the depth of penetration of x-rays from said target material, said x-ray diffraction line intensity profile of the member using said target material providing a measure of the average excess dislocation density of the member wherein the ratio of the average excess dislocation density of the member to the critical excess dislocation density of the member at fatigue failure is equivalent to the amount of fatigue damage which has occurred in the member.

2. The method of claim 1, wherein the x-rays of shallow penetrability are achieved by using chromium radiation from a chromium target in an x-ray tube.

3. The method of claim 1, wherein the member is formed of aluminum alloy and the x-rays of shallow penetrability are produced by selecting an x-ray target from a group consisting of chromium and copper.

4. The method of claim 1, wherein the work hardened surface layer in metallic materials extends up to a depth of from about 100 to about 200 micrometers and the x-rays have a depth of penetration of at least from about 200 to about 400 micrometers.

5. A method of determining the fatigue damage to a structural member which has undergone fatigue loading comprising the steps of:
   making an x-ray diffraction line intensity profile of the member to a depth of about 10 micrometers, said x-ray diffraction line intensity profile providing a measure of the critical excess dislocation density of the member at fatigue failure thereof; and
   making a second x-ray diffraction line intensity profile of the member from the surface to beyond the work hardened surface layer, which may extend to a depth of about 200 micrometers, said second profile being determined from x-ray diffraction patterns from sufficient depths to provide an average excess dislocation density of a desired accuracy wherein the x-ray diffraction line intensity profile of this step provides a measure of the average excess dislocation density of the member and wherein the ratio of the average excess dislocation density of the member of this step to the critical excess dislocation density of the member at failure is equivalent to the amount of fatigue damage which has occurred in the member.

6. A method of determining the stress-corrosion damage to a structural member comprising the steps of:
   making an x-ray diffraction line intensity profile of the member to a depth of about 10 micrometers, said x-ray diffraction line intensity profile providing a measure of the critical excess dislocation density of the member at stress-corrosion failure thereof; and
   making a second x-ray diffraction line intensity profile of the member from the surface to beyond the work hardened surface layer, which may extend to a depth of about 200 micrometers, said second profile being determined from x-ray diffraction patterns from sufficient depths to provide an average excess dislocation density of a desired accuracy wherein the x-ray diffraction line intensity profile of this step provides a measure of the average excess dislocation density of the member and wherein the ratio of the average excess dislocation density of the member of this step to the critical excess dislocation density of the member at failure is equivalent to the amount of stress-corrosion damage which has occurred to the member.

* * * * *